United States Patent [19]

Lambert

[11] Patent Number: 5,673,438
[45] Date of Patent: Oct. 7, 1997

[54] EAR SHIELD ASSEMBLY

[75] Inventor: Serge Lambert, 765 Amsterdam Ave. Apt. 10 H, New York, N.Y. 10025

[73] Assignee: Serge Lambert, New York, N.Y.

[21] Appl. No.: 703,694

[22] Filed: Aug. 27, 1996

[51] Int. Cl.$^6$ ..................................... A61F 11/14
[52] U.S. Cl. .................. 2/209; 2/174; 2/171; 128/857
[58] Field of Search ..................... 2/174, 203, 209, 2/171, 207; 128/857, 866, 867, 868

[56] References Cited

U.S. PATENT DOCUMENTS

| | | | |
|---|---|---|---|
| 1,851,455 | 3/1932 | Sjostrand | 2/174 |
| 1,878,397 | 9/1932 | Hekler et al. | 128/866 |
| 1,909,856 | 5/1933 | Dolder | 2/174 |
| 1,988,011 | 1/1935 | Margolith | 2/174 |
| 2,060,553 | 11/1936 | Burleigh | 2/174 |
| 2,424,352 | 7/1947 | Conjurske | 2/174 |
| 2,570,675 | 10/1951 | Helfin | 2/174 |
| 5,175,887 | 1/1993 | Kim | 2/207 |
| 5,423,091 | 6/1995 | Lange | 2/174 |

*Primary Examiner*—Jeanette E. Chapman
*Attorney, Agent, or Firm*—Michael Colitz, Jr.

[57] ABSTRACT

An ear shield assembly comprises a headband fabricated of semi-rigid material and formed in a generally semi-circular configuration, the headband having two free ends; and two ear covers each formed in a hollow generally semi-spherical configuration, each ear covering having a concave inner surface and a convex outer surface, a free end of the headband being coupled through each ear cover, in an operative orientation a user placing the headband across his forehead, the user then positioning each ear cover over the auricle of an ear, the apparatus protecting a user's forehead and ears from hair dye during hair coloring.

1 Claim, 3 Drawing Sheets

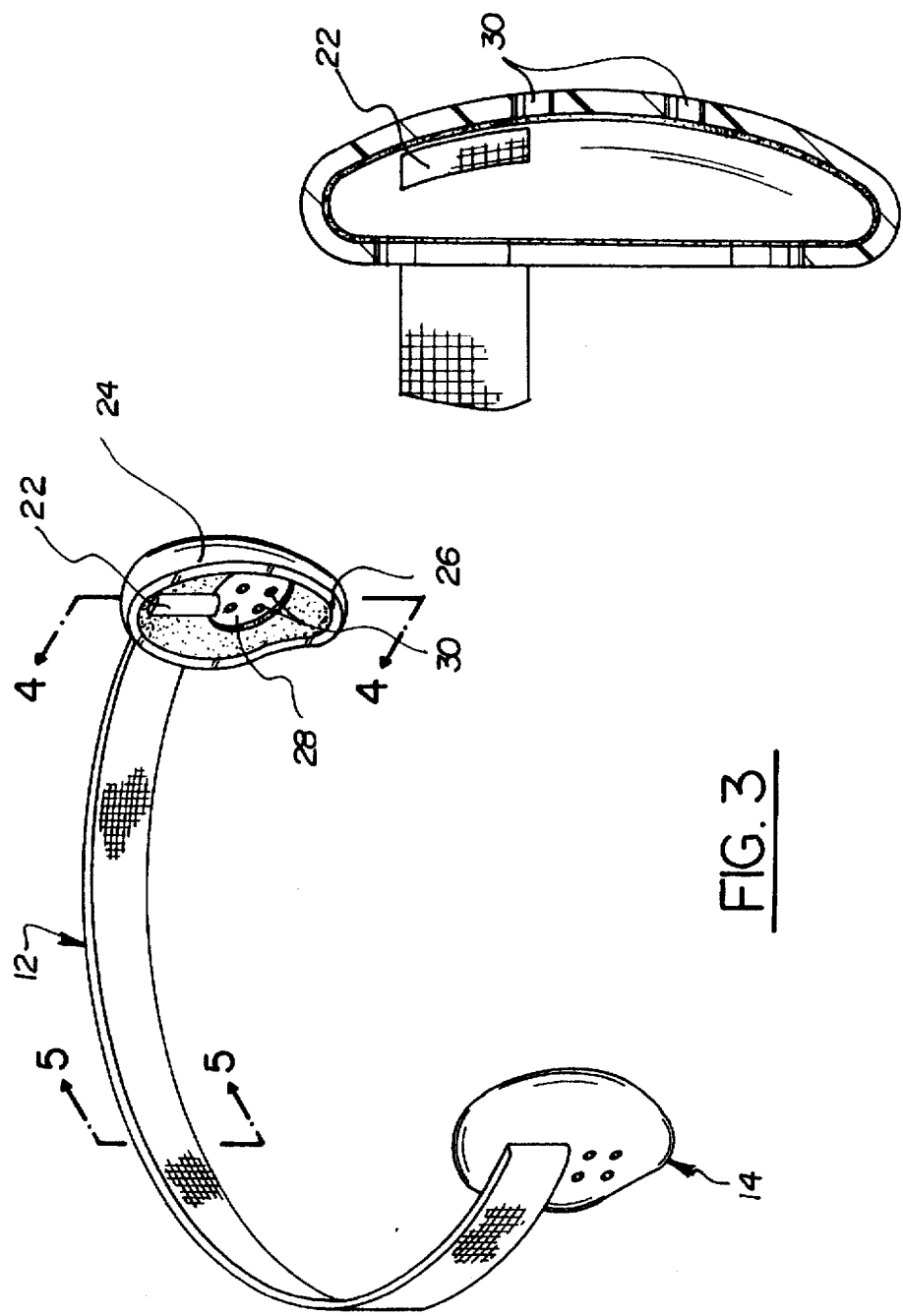

EAR SHIELD ASSEMBLY

BACKGROUND OF THE INVENTION

1. Field of the Invention

The present invention relates to an ear shield assembly and more particularly pertains to preventing hair dye from contacting a user's ears during hair coloring.

2. Description of the Prior Art

The use of head bands is known in the prior art. More specifically, head bands heretofore devised and utilized for the purpose of protecting a user's face from chemicals are known to consist basically of familiar, expected and obvious structural configurations, notwithstanding the myriad of designs encompassed by the crowded prior art which have been developed for the fulfillment of countless objectives and requirements.

By way of example, U.S. Pat. No. 4,958,385 to Rushton, Jr. discloses a hair dressing headband.

U.S. Pat. No. 4,368,545 to Seidman discloses a face protecting device.

U.S. Pat. No. Des. 355,047 to Grimes discloses a moisture retaining head band form use in permanent waving.

U.S. Pat. No. 5,175,887 to Kim discloses an absorbent headband.

U.S. Pat. No. 4,308,623 to Voorhees discloses a disposable fluid-tight ear protector.

U.S. Pat. No. 4,481,680 to Mason et al. discloses a protective visor.

While these devices fulfill their respective, particular objective and requirements, the aforementioned patents do not describe an ear shield assembly for preventing hair dye from contacting a user's ears during hair coloring.

In this respect, the ear shield assembly according to the present invention substantially departs from the conventional concepts and designs of the prior art, and in doing so provides an apparatus primarily developed for the purpose of preventing hair dye from contacting a user's ears during hair coloring.

Therefore, it can be appreciated that there exists a continuing need for new and improved ear shield assembly which can be used for preventing hair dye from contacting a user's ears during hair coloring. In this regard, the present invention substantially fulfills this need.

SUMMARY OF THE INVENTION

In the view of the foregoing disadvantages inherent in the known types of head bands now present in the prior art, the present invention provides an improved ear shield assembly. As such, the general purpose of the present invention, which will be described subsequently in greater detail, is to provide a new and improved ear shield assembly and method which has all the advantages of the prior art and none of the disadvantages.

To attain this, the present invention essentially comprises a new and improved ear shield assembly comprising, in combination: a headband formed in a planar rectangular configuration and shaped in a semi-circular orientation, the headband having a semi-rigid central section formed of absorbent sponge material, the headband having a fabric cover positioned around the central section, the headband having two free ends; and two ear covers each fabricated of plastic and formed in a hollow generally semi-spherical configuration with an upper section and a lower section, each ear covering having a concave inner surface and a convex outer surface, the lower section of each ear cover being tapered and having a smaller width than the upper section, each ear cover having a circular central portion with a plurality of holes extending therethrough, foam material being positioned upon the inner surface of each ear cover around the central portion, a free end of the headband being coupled through each ear cover above the central portion, in an operative orientation a user placing the headband across his forehead, the user then positioning the upper section of each ear cover over the helix of an ear and the lower section of each ear cover over the lobule of an ear, the apparatus protecting a user's forehead and ears from hair dye during hair coloring.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved ear shield assembly which has all the advantages of the prior art head bands and none of the disadvantages.

It is another object of the present invention to provide a new and improved ear shield assembly which may be easily and efficiently manufactured and marketed.

It is a further object of the present invention to provide a new and improved ear shield assembly which is of durable and reliable construction.

An even further object of the present invention is to provide a new and improved ear shield assembly which is susceptible of a low cost of manufacture with regard to both materials and labor, and which accordingly is then susceptible of low prices of sale to the consuming public, thereby making such an ear shield assembly economically available to the buying public.

Even still another object of the present invention is to provide a new and improved ear shield assembly for preventing hair dye from contacting a user's ears during hair coloring.

Lastly, it is an object of the present invention to provide a new and improved ear shield assembly comprises a headband fabricated of semi-rigid material and formed in a generally semi-circular configuration, the headband having two free ends; and two ear covers each formed in a hollow generally semi-spherical configuration, each ear covering having a concave inner surface and a convex outer surface, a free end of the headband being coupled through each ear cover, in an operative orientation a user placing the headband across his forehead, the user then positioning each ear cover over the auricle of an ear, the apparatus protecting a user's forehead and ears from hair dye during hair coloring.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 3 is a perspective view of the apparatus illustrating the inner surface of an ear cover.

FIG. 4 is a cross-sectional view of the apparatus taken along section line 4—4 of FIG. 3.

The same reference numerals refer to the same parts through the various Figures.

DESCRIPTION OF THE PREFERRED EMBODIMENT

Figure 1:
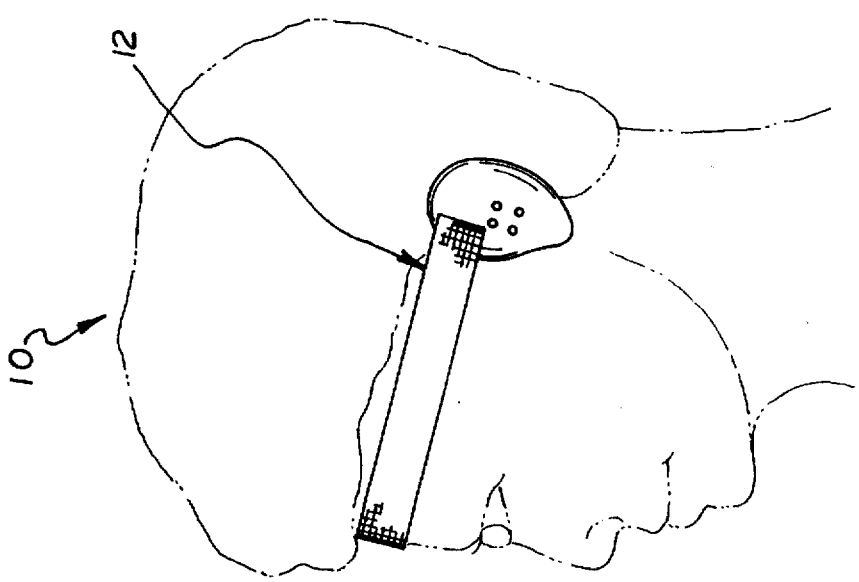
FIG. 1 is a perspective view of the preferred embodiment of the ear shield assembly constructed in accordance with the principles of the present invention.
Figure 6:
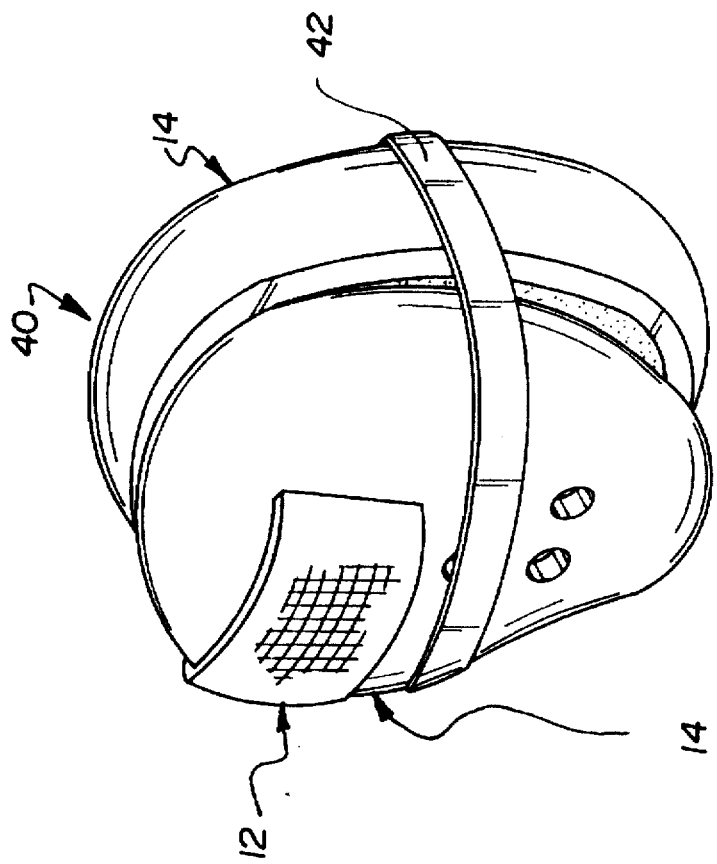
FIG. 6 is a perspective view of the apparatus in a stored orientation.

With reference now to the drawings, and in particular, to FIG. 1 thereof, the preferred embodiment of the new and improved ear shield assembly embodying the principles and concepts of the present invention and generally designated by the reference number 10 will be described.

Specifically, it will be noted in the various Figures that the device relates to an ear shield assembly 10. In its broadest context, the device consists of a headband 12 and two ear covers 14. Such components are individually configured and correlated with respect to each other so as to attain the desired objective.

Figure 2:
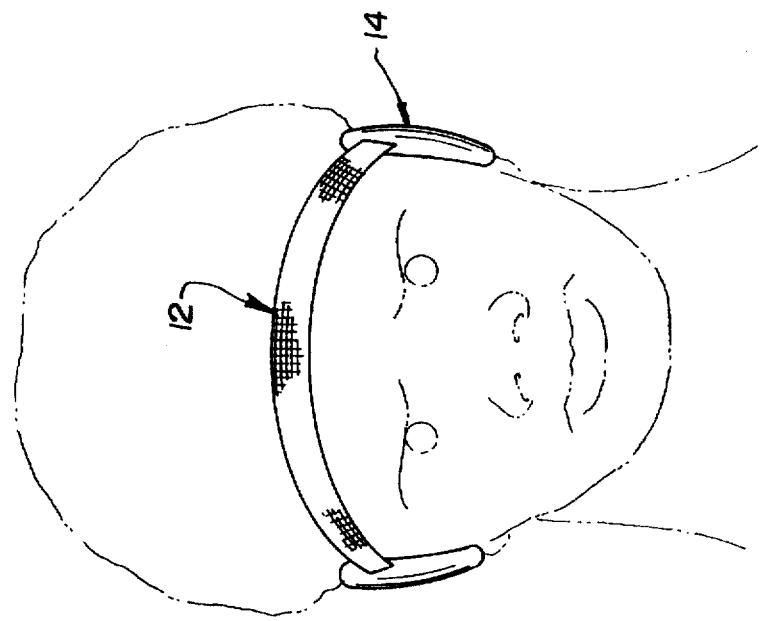
FIG. 2 is a front perspective view of the apparatus illustrating the head band.

The headband 12 is formed in a planar rectangular configuration and shaped in a semi-circular orientation. In the preferred embodiment of the apparatus the headband has a length of twelve inches. The headband has a semi-rigid central section 18 formed of absorbent sponge material. The headband has a fabric cover 20 positioned around the central section. This configuration allows a user to securely place the headband on his head while coloring his hair. The headband has two free ends 22. The absorbent sponge material absorbs any excess hair dye and protects a user's skin from the chemicals contained in the hair dye. After each use, the apparatus can be washed and reused. Note FIGS. 1, 2 and 5.

Two ear covers 14 are included with the apparatus. Each ear cover is fabricated of plastic and formed in a hollow generally semi-spherical configuration with an upper section 24 and a lower section 26. In the preferred embodiment of the apparatus each ear cover has a height of three inches and a central width of one and one-half inches. In varying embodiments of the apparatus, the ear covers are formed in a variety of sizes. Each ear cover has a concave inner surface and a convex outer surface. The lower section of each ear cover is tapered and has a smaller width than the upper section. Each ear cover is shaped similarly to the auricle of a human ear. Each ear cover has a circular central portion 28 with a plurality of holes 30 extending through it. The holes allow a user to hear while wearing the apparatus. Note FIGS. 3 and 4.

Foam material 32 is positioned upon the inner surface of each ear cover around the central portion. The foam material provides comfort to the user while wearing the apparatus. A free end of the headband is coupled through each ear cover above the central portion. In an operative orientation a user places the headband across his forehead. The user then positions the upper section 24 of each ear cover over the helix of his ear and the lower section 26 of each ear cover over the lobule of his ear. The apparatus protects a user's forehead and ears from hair dye during hair coloring. This apparatus minimizes the time required for hair coloring since it obviates the need for a user to constantly remove hair dye from his face and ears. This prevents a user from having to spend extra time cleaning up. Note FIGS. 1–4.

Figure 5:
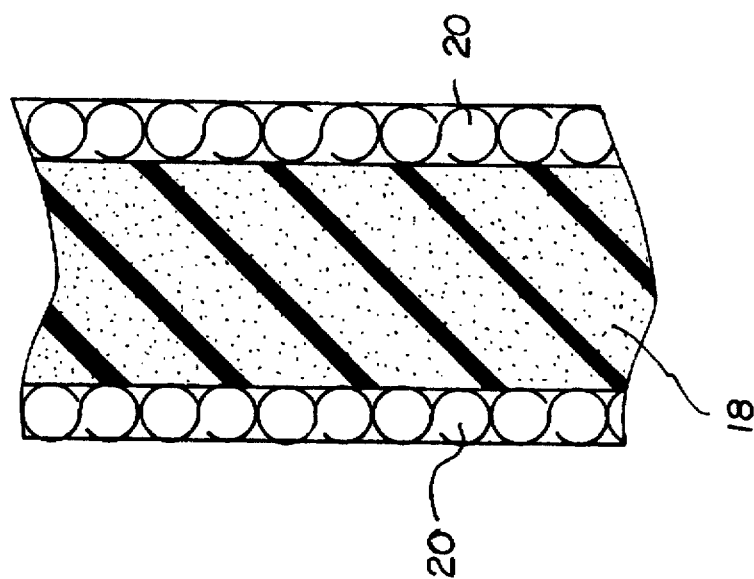
FIG. 5 is a cross-sectional view of the apparatus taken along section line 5—5 of FIG. 3.

As can be seen in FIG. 5, the apparatus also has a stored orientation 40. In such orientation, the inner surfaces of the ear covers are in engaging contact with the each other. The headband is wrapped around the ear covers. The apparatus is secured with a rubber band 42. This orientation requires very little storage space. Note FIG. 5.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and the manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modification and changes will readily occur to those skilled in the art, it is not desired to limit the invention to the exact construction and operation shown and described, and accordingly, all suitable modification and equivalents may be resorted to, falling within the scope of the invention.

What is claimed as being new and desired to be protected by Letters Patent of the United States is as follows:

1. A new and improved ear shield assembly comprising, in combination:

a headband formed in a planar rectangular configuration and shaped in a semi-circular orientation, the headband having a semi-rigid central section formed of absorbent sponge material, the headband having a fabric cover positioned around the central section, the headband having two free ends, a user securely placing the headband on his head; and two ear covers each fabricated of plastic and formed in a hollow generally semi-spherical configuration with an upper section and a lower section, each ear covering having a concave inner surface and a convex outer surface, the lower section of each ear cover being tapered and having a smaller width than the upper section, each ear cover being shaped similarly to the auricle of a human ear, each ear cover having a circular central portion with a plurality of holes extending therethrough, foam material being positioned upon the inner surface of each ear cover around the central portion, a free end of the headband being coupled through each ear cover above the central portion, in an operative orientation a user placing the headband across his forehead, the user then positioning the upper section of each ear cover over the helix of an ear and the lower section of each ear cover over the lobule of an ear, the apparatus protecting a user's forehead and ears from hair dye during hair coloring.

* * * * *